(12) United States Patent
Davis et al.

(10) Patent No.: US 7,303,143 B2
(45) Date of Patent: Dec. 4, 2007

(54) WICK ASSEMBLY

(75) Inventors: Brian T. Davis, Burlington, WI (US);
Robert R. Emmrich, Racine, WI (US);
Kenneth J. Welch, Racine, WI (US);
Padma P. Varanasi, Racine, WI (US);
Joel E. Adair, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 421 days.

(21) Appl. No.: 10/875,342

(22) Filed: Jun. 24, 2004

(65) Prior Publication Data

US 2005/0284952 A1   Dec. 29, 2005

(51) Int. Cl.
*A24F 25/00*   (2006.01)

(52) U.S. Cl. ............... 239/44; 239/45; 239/43; 239/55; 239/145; 239/326; 239/49; 431/325

(58) Field of Classification Search ........... 239/45, 239/44, 55, 56, 60; 431/325
See application file for complete search history.

(56) References Cited

U.S. PATENT DOCUMENTS

| | | | |
|---|---|---|---|
| 1,129,897 A * | 3/1915 | Owen, Jr. ............ 239/45 |
| 3,262,290 A | 7/1966 | Huber | |
| 3,746,255 A | 7/1973 | Surloff .............. 239/51.5 |
| 4,286,754 A * | 9/1981 | Jones ................. 239/6 |
| 4,416,616 A | 11/1983 | Shimizu et al. | |
| 4,663,315 A | 5/1987 | Hasegawa et al. | |
| 4,915,301 A * | 4/1990 | Munteanu ............ 239/45 |
| 5,014,913 A * | 5/1991 | Hoyt et al. .......... 239/45 |
| 5,038,394 A | 8/1991 | Hasegawa et al. | |
| 5,095,647 A | 3/1992 | Zobele et al. | |
| 5,222,186 A | 6/1993 | Schimanski et al. | |
| 5,290,546 A | 3/1994 | Hasegawa et al. | |
| 5,437,832 A * | 8/1995 | Imamura et al. ........ 419/2 |
| 5,647,053 A | 7/1997 | Schroeder et al. | |
| 5,725,152 A * | 3/1998 | Akyu ................. 239/45 |
| 6,196,832 B1 * | 3/2001 | Mifune et al. ........ 431/129 |
| 6,361,752 B1 | 3/2002 | Demarest et al. | |
| 6,426,051 B1 | 7/2002 | Allison | |
| 6,786,427 B2 * | 9/2004 | Schram et al. ........ 239/145 |
| 2003/0161755 A1 | 8/2003 | Richards ............. 422/5 |

FOREIGN PATENT DOCUMENTS

| EP | 897 755 A2 | 2/1999 |
|---|---|---|
| WO | WO 2004/084959 A1 | 10/2004 |
| WO | WO 2005/002636 A1 | 1/2005 |

OTHER PUBLICATIONS

U.S. Appl. No. 10/354,876, filed Jan. 30, 2003.

* cited by examiner

*Primary Examiner*—Dinh Q. Nguyen

(57) ABSTRACT

A wick assembly is provided for use in a dispensing device that dispenses volatile material from a wick by heat. Two wick sections of differing material are provided in stacked fashion, with a coupler sleeve that can be used to facilitate attachment of the wick structure to a reservoir. One wick section preferably provides control over the rate of dispensing, where the other provides improved thermal resistance and resistance to clogging.

11 Claims, 3 Drawing Sheets

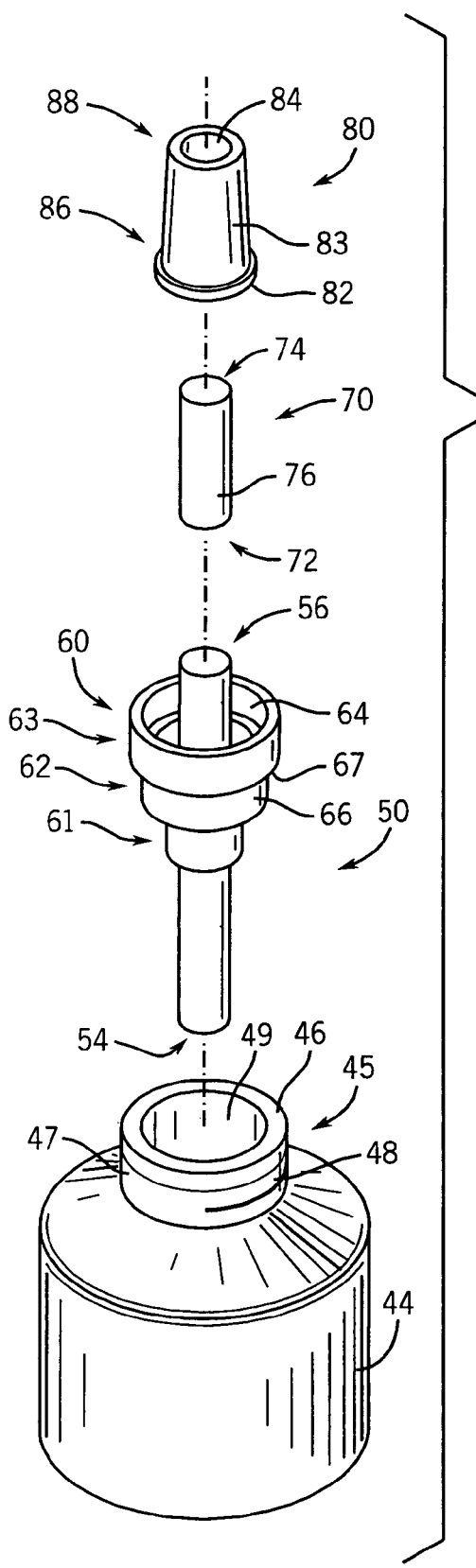
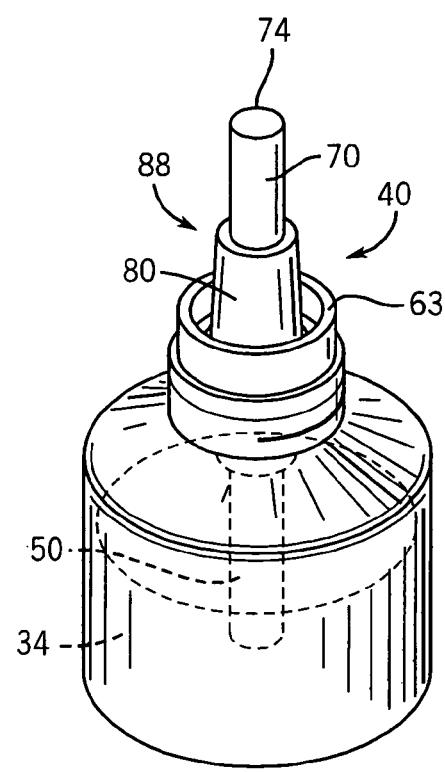
FIG. 3
FIG. 4

WICK ASSEMBLY

CROSS-REFERENCES TO RELATED APPLICATIONS

Not applicable.

STATEMENT REGARDING FEDERALLY SPONSORED RESEARCH

Not applicable.

BACKGROUND OF THE INVENTION

This invention relates to dispensing devices that employ a heat source to promote the release of a volatile material from a wick. More particularly, the invention relates to improved wick assemblies for use with such devices.

A variety of devices for dispensing volatizable materials into the atmosphere are known. Such volatizable materials may be air scents (e.g. fragrances), pest control materials (e.g., insecticides), allergen control ingredients, disinfectants, or other chemicals.

In one such type of device a lower reservoir is provided into which a wick extends. The wick draws the active chemical up from the reservoir to an area where there is a heat source. The heat source then promotes dispensing of the volatile to the environment. Such devices are plugged into an electrical wall outlet to supply power to an electrical heating coil. Optionally, such devices may also have a fan or other means to further promote evaporation or dispensing.

Prior art examples of such devices include U.S. Pat. Nos. 6,361,752, 5,647,053, 5,290,546, 5,222,186, 5,095,647, 5,038,394, and 4,663,315. The disclosure of these patents and all other publications referred to herein, are incorporated herein by reference as if fully set forth.

While the foregoing prior art devices have a number of advantages, they also have some deficiencies, particularly with respect to the wicks used with them. For example, when some of these devices are used to dispense certain volatile materials, certain wicks can clog. Other wicks are less susceptible to clogging, but are too brittle to use in certain automated assembly operations. Still other wicks tend to draw liquid too fast, creating a "drool" problem or inefficient use of certain actives. Some other wicks are not sufficiently thermally resistant to use with some types of heating devices.

One improvement is described in a U.S. patent application (of our assignee) filed on Jan. 30, 2003 with U.S. Ser. No. 10/354,876. That application disclosed providing an array of granular particles such as sand coated with a polymer binder to form a network of pores in the wick which were less susceptible to clogging. However, this type of wick was not physically strong enough to resist the mechanical stresses encountered in some automated assembly operations. This added some cost to the assembly of such wicks with devices that use them.

In unrelated work there have been some disclosures of certain types of multi-part wicks. See e.g. U.S. Pat. Nos. 4,416,616 and 3,262,290 and European Patent Application No. EP 0 897 755 A2. However, these wick constructions have not been suggested as a solution to the above problems, and in any event the means of associating the wick parts are not desirable for the present applications.

Thus, there is a need for improved wick assemblies that address the above deficiencies of the prior art.

SUMMARY OF THE INVENTION

In one aspect, the invention provides a wick assembly for use in a dispensing device that is capable of dispensing volatile material from a reservoir containing that volatile material. The assembly has a first wick section formed from a first material, and a second wick section formed from a second material that includes granules bound together by a binder and that is different from the first material. The second wick section is positioned abutting against or adjacent to the first wick section (e.g. in axially vertically stacked fashion).

There is also a coupling sleeve for holding the second wick section against, or adjacent to, the first wick section, and means for mounting the coupling sleeve to the reservoir with the first wick section extending into the reservoir. One such mounting means is providing a radially extending flange adjacent a lower end of the sleeve, and providing a cap ring mountable on the reservoir which can receive the flange in a depressed annular bore. Other such means include any other means of attaching the sleeve to the reservoir (e.g. mechanical means for directly attaching the sleeve to the reservoir such as spring legs; adhesive attachment of the sleeve to the cap ring or reservoir; etc.).

In the most preferred form the second wick section is formed from sand particles and a binder (which creates a thermal resistant, clog resistant high flow section around which the heater will be positioned), and the first wick section is formed from a material selected from the group consisting of fibrous materials, wood products, plastic particles, and inorganic particles (which creates a section capable of precise flow control). The second wick section is insertable through a central through bore of a cap ring. Alternatively, the cap ring can be integral with the first wick section. The coupling sleeve has a tapering internal bore, and both the first and second wick sections are essentially cylindrical.

In an alternative form the invention provides a wick assembly for use in a dispensing device that is capable of dispensing volatile material from a reservoir containing that volatile material. This wick assembly has a first wick section formed from a plastic material, and a second wick section formed from a composition comprising sand and a binder. The second wick section is positioned abutting against or adjacent to the first wick section, preferably in vertically stacked fashion.

In yet another form the invention provides a method for assembling a wick assembly. One obtains wick assembly components comprising a cap ring, a first wick section made of a first material, a second wick section made of a second wick material, and a coupling sleeve. One then inserts the second wick section into the coupling sleeve such that an end of the second wick section terminates inside the coupling sleeve and an opposed end of the second wick section terminates outside the coupling sleeve. One also inserts the first wick section into the cap ring so that an end of the first wick section terminates on one side of the cap ring, and an opposed end of the first wick section terminates on an opposed side of the cap ring. Thereafter, one assembles a sub-combination of the second wick section and coupling sleeve to a sub-combination of the second wick section and cap ring.

The wick assemblies of the present invention are preferably used with a ring heater. They may also be used with a fan that facilitates dispensing from the upper portion of the wick.

The structures of the present invention have a number of advantages. For one thing, a highly thermally and clog resistant sand based wick section can be used adjacent such heaters. Any concerns about the brittleness of sand based wick sections are addressed by the method of insertion of that wick portion into a tapered coupler, minimizing the stress on the wick due to the insertion.

Moreover, any tendency of that wick portion to draw fluid too quickly (and thus lead to drool or inefficient dispensing) is controlled by the first wick segment, which can have carefully sized pores. Further, any tendency of the first wick portion to degrade when exposed to heat is avoided as that portion is positioned away from the heater.

Desirably, the same second wick portion can be used with a variety of different first wick portions, depending on the particular chemicals involved and the dispensing needs. Thus, a single sand based wick portion can be made suitable for use with a wide variety of applications, thus reducing production costs by avoiding the need to make multiple different sand wicks.

Moreover, the assembly is suitable for using high speed automated assembly equipment. This further reduces the costs.

These and still other advantages of the present invention will be apparent from the description which follows and the accompanying drawings. While preferred embodiments will be disclosed in connection therewith, it should be appreciated that still other embodiments are possible within the spirit of the invention. Hence, the claims should be looked to in order to judge the full scope of the invention.

BRIEF DESCRIPTION OF THE DRAWINGS

FIG. 3 is an exploded perspective view of a device according to the invention;

FIG. 4 is a perspective view of the device of FIG. 3 in assembled form; and

DETAILED DESCRIPTION OF THE INVENTION

Figure 1:
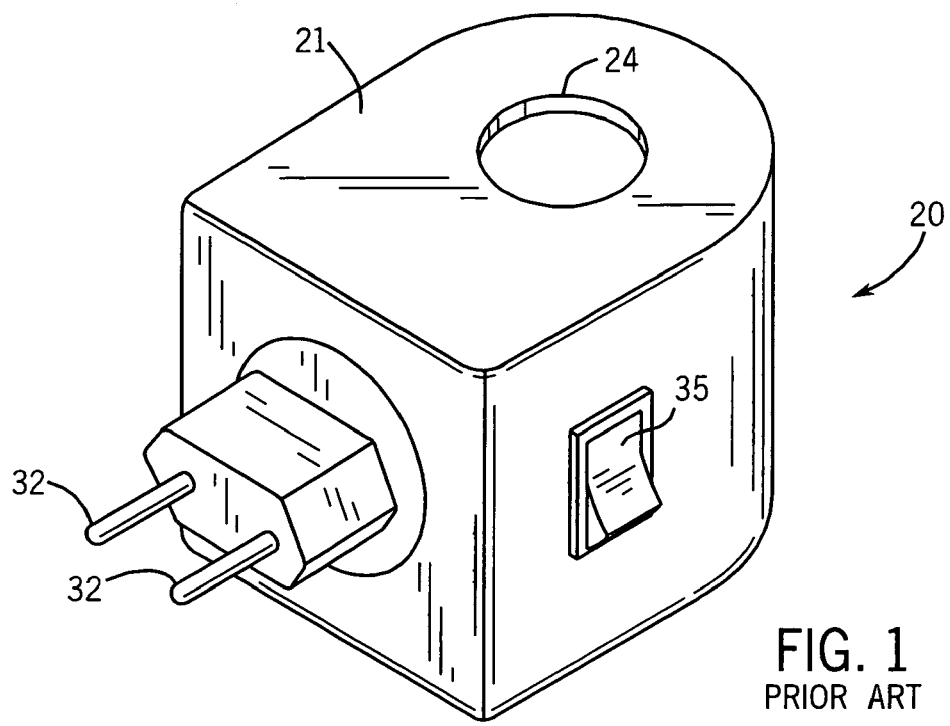
FIG. 1 is a perspective view showing a prior art device for dispensing volatile materials.
Figure 2:
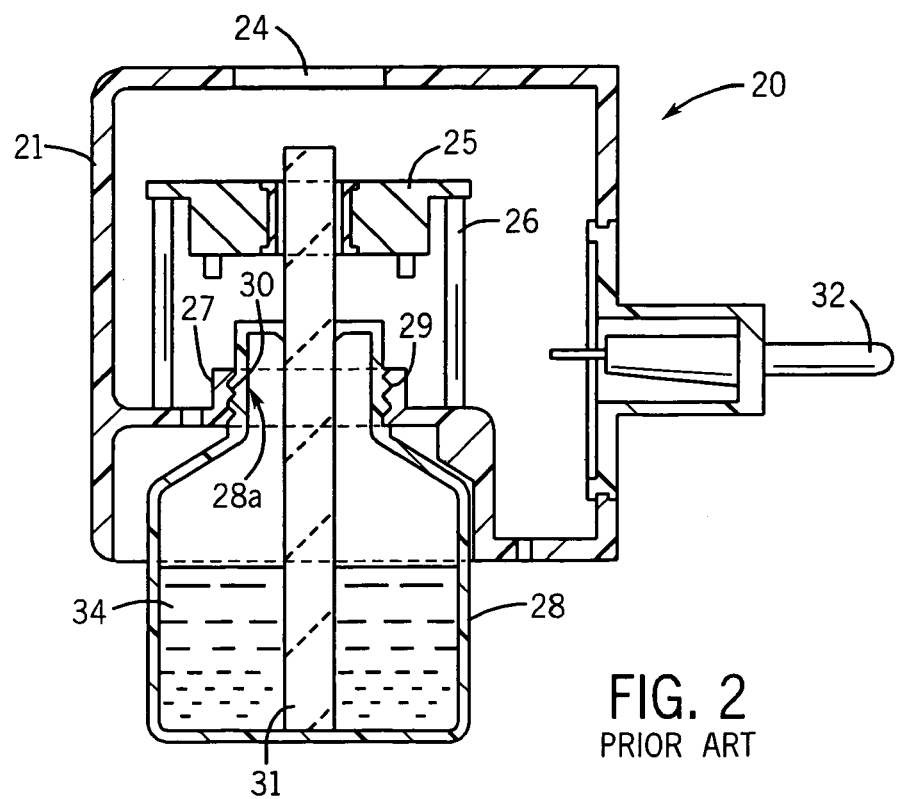
FIG. 2 is a vertical cross-sectional view of the device of FIG. 1 having installed therein a prior art wick and liquid reservoir.

Referring to FIGS. 1 and 2, there is shown a prior art dispensing device 20 in which a heat source is used to promote the wicking action and release of a volatile material from a wick immersed in a volatile liquid contained in a reservoir. The dispensing device 20 includes a body 21 having a vapor outlet 24 formed in the center of the top of the body 21. A ring heater 25 having an opening extending vertically there through is provided inside the body 21 below the vapor outlet 24. The ring heater 25 is supported by a stay 26. Provided under the heater 25 is a bottle socket 27 having an opening extending vertically there through. The socket 27 is formed on its inner periphery with a threaded portion 30 adapted for threaded engagement with a threaded portion 29 on the outer periphery of the mouth 28a of a volatile liquid bottle 28.

The bottle 28 is provided with a wick 31 that is insertable into the ring heater 25 concentrically therewith when the bottle 28 is threaded at its mouth 28a into the socket 27. The wick 31 is immersed in the liquid 34 in the bottle 28 and upwardly transports the liquid 34 contained in the bottle 28 by capillary action. The wick 31 in this prior art design was formed from a fired porous ceramic or a sintered plastic material.

Electrical plug blades 32 are fixed to the body 21 on its rear side. The plug blades 32 are connected to the ring heater 25 in the usual manner using electrical connections. The ring heater 25 is energized by inserting the plug blades 32 into an electrical outlet and activating switch 35, whereby the ring heater 25 produces heat to heat the upper section of the wick 31. The heat may promote upward transport of the liquid 34 in the wick 31. The liquid chemical 34 in the wick 31 is vaporized by the heat from the ring heater 25. For other designs of this general type see e.g. U.S. Pat. No. 5,290,546.

Figure 5:
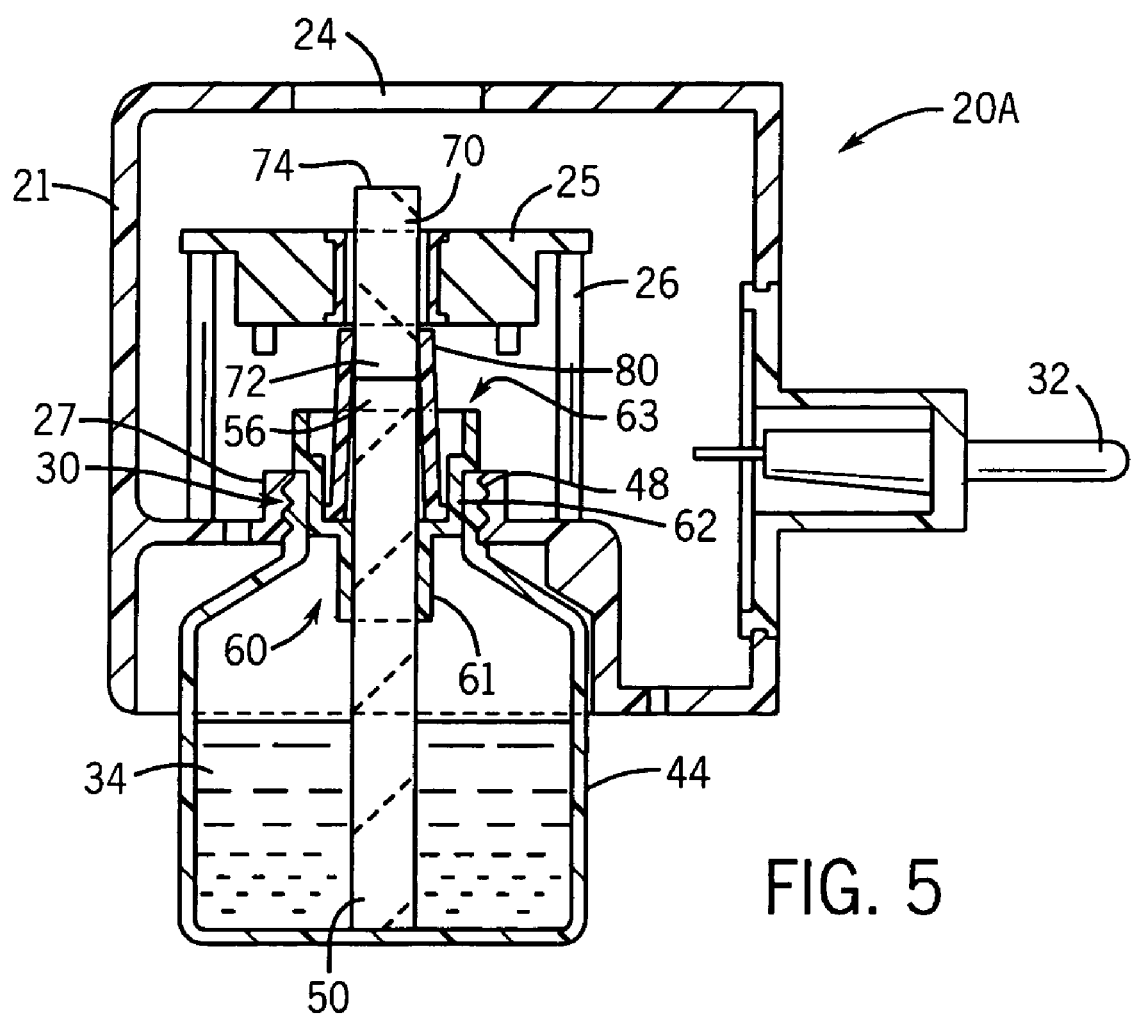
FIG. 5 is a cross-sectional view similar to FIG. 1, but of the present invention.

Turning now to FIGS. 3, 4 and 5, there is shown a device constructed in accordance with the present invention. There is a wick assembly 40 and a reservoir 44 suitable for use in a heated volatile dispensing device analogous to that shown in FIGS. 1 and 2. Where the parts are numbered the same, the parts numbered in FIGS. 3-5 are essentially identical to the parts of FIGS. 1 and 2. The reservoir 44 includes a mouth 45 having an inner surface 49 and an outer surface 47 with threads 48. A rim 46 of the mouth 45 defines an opening for the reservoir 44. The reservoir 44 can be formed from a thermoplastic material such as polyethylene, polypropylene or polyethylene terephthalate, albeit a glass reservoir is often preferred to provide a consumer with an easy view of how much liquid is left in the reservoir.

The wick assembly 40 includes a lower wick section 50, a cap ring 60, an upper wick section 70 and a coupling sleeve 80. The lower wick section 50, the cap ring 60, the upper wick section 70 and the coupling sleeve 80 are assembled together as described below.

The lower wick section 50 may be formed in any number of shapes. In the example embodiment shown the wick section 50 is in the shape of an elongated cylinder. The wick section 50 may be formed from fibrous materials, wood products, thermoplastic particles and inorganic particles. Non-limiting examples of fibrous materials include bonded polyester fibers, cellulose, carbon fibers or the like. Non-limiting examples of wood products include compressed sawdust or wood flour. Non-limiting examples of thermoplastic particles include particles that may be sintered into a porous body.

However, preferred materials for the wick section 50 are polyolefins such as polyethylene and polypropylene, and thermoplastic polyesters. A particularly preferred plastic is an ultra-high molecular weight high density polyethylene from Porex Technologies. Such plastics can be lightly packed into a mold, and the packed mold can then be heated to a temperature which is sufficient to allow the thermoplastic particles to bond together, but not sufficient to liquefy the thermoplastic to such an extent that it can flow. This results in a solid wick that is porous and therefore wicks liquid.

Alternatively, wick section 50 could be formed of inorganic particles such as kaolin, clay, talc, perlite, bentonite, alumina, alumina silica, titania or the like. The inorganic powder particles can be lightly packed into a mold, and the packed mold can then be heated to a temperature which is sufficient to allow the powdered particles to bond together at contact points. This results in a solid wick that is porous and therefore wicks liquid.

The upper wick section 70 may be formed in any number of shapes, and in the example embodiment shown is in the shape of an elongated cylinder. The most preferred upper wick section 70 comprises sand particles adhered together by a binder to form a network of pores and passages. In one example method for making the upper wick section 70, individual sand particles can be coated with a thin coating of the binder. The coated sand particles are then placed in a mold and compacted under elevated temperature conditions. The binder coated on the particles flows to form a thin coating on the individual particles, with the coatings fused together at their points of contact. The binder only partially fills the interstices between the particles, whereby an interconnected network of pores and passages is formed.

The sand particles may comprise silica sand particles, chromite sand particles, zircon sand particles, and mixtures thereof. Silica sand particles are typically preferred because an upper wick section 70 formed using silica sand particles has superior fluid transport properties. Spherical particles are the preferred particles because of the greater uniformity in porosity achieved and because rounded particles can be closely packed together.

A number of different binders can be used to adhere the sand particles together. Thermoset polymeric materials, i.e., materials that become relatively infusible upon heating, are preferred for the binder because these cross-linking polymeric materials will not flow when the formed upper wick section 70 is heated in a dispensing device. If the binder were to flow excessively upon heating, clogging of the network of pores and passages could result. However, as used herein, the term "thermoset polymeric material" is not limited to traditional thermosetting materials but also encompasses cross linked thermoplastic materials that chemically react to become relatively infusible upon heating.

The most preferred binder material is a novolac resin. Other non-limiting examples of thermoset binder materials include urethane resins and highly cross linked thermoplastics such as cross linked polyethylene. Furthermore, most polymeric materials can be used to bind the sand particles together, so long as the polymeric material is non-reactive and non-absorptive with respect to the volatile material to be dispensed and the polymeric material can resist the temperatures to which the upper wick section 70 will be exposed in the dispensing device.

Because sand particles individually coated with the binder are flowable until adhered into a upper wick section 70, they may be introduced into molds of various sizes and shapes and heated to form virtually any shape structure for the upper wick section 70. Advantageously, the sand particles may be purchased pre-coated. For example, resin coated sand particles are available from Technisand Division of Fairmount Minerals, Wedron, Ill., USA. One type of commercially available resin coated sand comprises a phenol formaldehyde novolac resin (1-6% by total weight) and a hexamethylenetetramine curing agent (<2% by total weight) coated on an aggregate including iron oxides (<15% by total weight), aluminum silicate (<15% by total weight) and silica sand (i.e., quartz). Another type of commercially available resin coated sand comprises a phenol formaldehyde novolac resin and a hexamethylenetetramine curing agent coated on chromite sand. Yet another type of commercially available resin coated sand comprises a phenol formaldehyde novolac resin and a hexamethylenetetramine curing agent coated on zircon sand.

A method of forming the upper wick section 70 from a novolac resin coated silica sand will now be described. The novolac resin coated silica sand is low pressure injected into a heated mold at 300° F.-700° F. to form the upper wick section 70. The mold heat completes the irreversible cross-linking of the novolac resin. Preferably, the network of pores and passages formed occupies at least 25 to 30% by volume percent of the upper wick section 70, and most preferably, the network of pores and passages formed occupies at least 40% by volume percent of the upper wick section 70. Preferably, the average pore size is in the range of 20 to 200 microns, and most preferably, the average pore size is in the range of 4 to 100 microns. In one form, the upper wick section 70 may have different densities at different regions of the substrate.

Still referring to FIGS. 3-5, the lower wick section 50 is positioned in the mouth 45 of the reservoir 44 through a central path of the cap ring 60. The cap ring 60 has a lower tubular collar section 61, a middle collar 62 with an outer surface 66, and an upper collar 63 with a lower surface 67, which help define the path. The lower wick section 50 may be held in place in the cap ring 60 by way of an interference fit with inner surfaces of the lower tubular collar 61, the middle collar 62 and the upper collar 63. Alternatively, the lower wick section may be integral with the cap ring 60. Preferably, the cap ring 60 is formed from a thermoset or thermoplastic polymeric material such as a polyolefin, a polyester or a polyamide, albeit separate formation is preferred to avoid the cap ring 60 being made of a porous material (thereby avoiding lateral capillary action).

When the lower wick section 50 is held in place in the cap ring 60, an annular depression 64 forms between the lower wick section 50 and the upper collar 63 and middle collar 63 of the cap ring 60. The lower wick section 50 and the cap ring 60 are assembled to the reservoir 44 by an interference fit between the outer surface 66 of the middle collar 62 and the inner surface 49 of the mouth 45 of the reservoir 44. The lower surface 67 of the upper collar 63 also rests on the rim 46 of the mouth 45 of the reservoir 44 as shown in FIGS. 4 and 5. When the lower wick section 50 and the cap ring 60 are assembled to the reservoir 44, the lower end 54 of the lower wick section 50 is immersed in liquid 34 in the reservoir 44, and the upper end 56 of the lower wick section 50 extends above the upper collar 63.

The lower end 72 of the upper wick section 70 is held in abutting or adjacent relationship to the upper end 56 of the lower wick section 50 by way of the coupling sleeve 80. The coupling sleeve 80 includes an annular base 82 and a tubular section 83 that extends upward from the annular base 82. The tubular section 83 of the coupling sleeve 80 has an inner diameter that decreases from a bottom end 86 of the tubular section 83 of the coupling sleeve 80 to a top end 88 of the tubular section 83 of the coupling sleeve 80. Thus, the inner surface 84 of the tubular section 83 tapers inward from the bottom end 86 of the coupling sleeve 80 to the top end 88 of the coupling sleeve 80. Preferably, the coupling sleeve 80 is formed from a thermoset or thermoplastic polymeric material such as a polyolefin, a polyester or a polyamide.

The upper wick section 70 is inserted up into the annular base 82 of the coupling sleeve 80 and moved toward the top end 88 of the coupling sleeve 80. The outer surface 76 of the upper wick section 70 then forms an interference fit with the inner surface 84 of the tubular section 83 of the coupling sleeve 80. However, the points of contact are limited due to the tapering, thereby reducing the stress on the sand wick caused by the insertion. When the upper wick section 70 and the coupling sleeve are assembled, the upper end 74 of the upper wick section 70 extends beyond the top end 88 of the coupling sleeve 80 as shown in FIG. 4, and an opposite end of the upper wick section 70 terminates inside the coupler. This creates a first subassembly.

Separately, the lower wick section 50 can be positioned in the cap ring 60 such that opposed ends 54 and 56 extend beyond the ring on opposite sides thereof. This is a second subassembly.

The annular base 82 of the coupling sleeve 80 is then press fit in the annular depression 64 between the lower wick section 50 and the upper collar 63 and middle collar 62 of the cap ring 60 such that the lower end 72 of the upper wick section 70 is held in abutting or adjacent relationship to the upper end 56 of the lower wick section 50. It should be appreciated that while this method of assembly is preferred for the use of automated equipment, the wick 40 and the reservoir 44 may be assembled in suitable alternative sequences.

The above structure may be installed in/on the volatile dispensing device 20A as shown in FIG. 5. Specifically, the threads 48 on the outer surface 47 of the mouth 45 of the reservoir 44 may be engaged with the threaded portion 30 on the inner surface of the bottle socket 27 of the volatile dispensing device 20A by rotating the reservoir 44. When the wick 40 and reservoir 44 are installed in the volatile dispensing device 20A, the upper wick section 70 is positioned in the opening in the ring heater 25 of the volatile dispensing device 20A, the coupling sleeve 80 is positioned below the ring heater 25, and the upper end 56 of the lower wick section 50 is positioned below the ring heater 25.

In operation of the volatile dispensing device 20A, the lower wick section 50 is immersed in the liquid 34 in the reservoir 44 and therefore upwardly transports the liquid 34 contained in the reservoir 44 by capillary action. The liquid 34 reaches the upper end 56 of the lower wick section and enters the lower end 72 of the upper wick section 70. Preferably, the upper end 56 of the lower wick section 50 and the lower end 72 of the upper wick section 70 abut each other to facilitate liquid transfer between the upper end 56 of the lower wick section 50 and the lower end 72 of the upper wick section 70. However, the upper end 56 of the lower wick section 50 and the lower end 72 of the upper wick section 70 may be spaced apart in adjacent relationship as long as liquid transfer between the upper end 56 of the lower wick section 50 and the lower end 72 of the upper wick section 70 is possible.

The upper wick section 70 then upwardly transports by capillary action the liquid 34 received from the lower wick section 50. The ring heater 25 produces heat to heat the upper wick section 70. The liquid 34 in the upper wick section 70 is vaporized by the heat from the ring heater 25 and enters the surrounding air.

The liquid to be dispensed is inserted in the reservoir 44 prior to mounting the wick assembly on the reservoir. Where the liquid is an insect control ingredient, the active can be selected from the group consisting of insecticides, insect repellents, and insect growth control ingredients. Examples include organic phosphorous insecticides, lipidamide insecticides, natural repellents as citronella oil, natural pyrethrins and pyrethrum extract, and synthetic pyrethroids are preferred. Suitable synthetic pyrethroids are acrinathrin, allethrin as D-allethrin, Pynamin®, benfluthrin, bifenthrin, bioallethrin as Pynamin Forte®, S-bioallethrin, esbiothrin, esbiol, bisoresmethrin, cyclopothrin, cyfluthrin, beta-cyfluthrin, cyhalothrin, lambda-cyhalothrin, cypermethrin, alpha-cypermethrin, beta-cypermethrin, cyphenothrin, deltamethrin, empenthrin, esfenvalerate, fenpropathrin, fenvalerate, flucythrinate, taufluvalinate, kadethrin, permethrin, phenothrin, prallethrin as Etoc®, resmethrin, tefluthrin, tetramethrin, tralomethrin, or transfluthrin.

When the present invention is used for the purpose of delivering fragrance, various natural and artificial perfumes may be used. Non-limiting examples of these perfumes include animal-based and plant-based natural perfumes, and artificial perfumes such as alcohols, phenols, aldehydes, ketones, terpenes, and esters.

The choice of volatile material or mixtures of volatile materials may depend on the temperatures provided by the dispensing device. For instance, the heated volatile dispensing device 20A of FIG. 5 may typically produce a wick surface temperature of about 100° C. when used with insecticides. Therefore, the volatile material or mixture of volatile materials is selected to provide an efficient release of the volatile materials from the upper wick section 70.

One particular formulation of active can be prepared by mixing the following ingredients in Table 1. A heater temperature of about 140° F. is preferred for volatilizing that formulation.

TABLE 1

| Weight Percent of Formulation | Common name or commercial name | Chemical name | Function in the formulation |
|---|---|---|---|
| 2.5% | Pyrethrum Extract, 50% | pyrethrins | insecticide |
| 1.2% | ETOC | prallethrin | insecticide |
| 2.0% | BHT | butylated hydroxy toluene | antioxidant |
| 1.0% | Takasago 35787 | fragrance mixture | aroma |
| 93.3% | Isopar-V | isoparaffinic hydrocarbon | solvent |

Although the present invention has been described in considerable detail with reference to certain embodiments, one skilled in the art will appreciate that the present invention can be practiced by other than the described embodiments, which have been presented for purposes of illustration and not of limitation. For example, the sleeve could be coupled directly to the reservoir with a lower wick of multiple diameters positioned against the upper wick. Therefore, the scope of the appended claims should not be limited to the description of the embodiments contained herein.

INDUSTRIAL APPLICABILITY

The invention relates to dispensing devices for delivering volatile materials from improved wick structures.

We claim:

1. A wick assembly for use in a dispensing device that is capable of dispensing volatile material from a reservoir containing that volatile material, the wick assembly comprising:
   a first wick section formed from a first material;
   a second wick section formed from a second material that includes granules bound together by a binder and that is different from the first material, wherein the second wick section is positioned abutting against or adjacent to the first wick section;
   a coupling sleeve for holding the second wick section against, or adjacent to, the first wick section so that ends of both the first and second wick sections terminate in the coupling sleeve and the coupling sleeve holds the wick sections in that abutting or adjacent relationship, wherein the coupling sleeve has a tapering internal bore and both the first and second wick sections terminate in the tapering internal bore; and means for mounting the coupling sleeve to a reservoir so that the first wick section can extend into the reservoir;

wherein one of said wick sections has an outer surface that forms an interference fit with the tapering internal bore of the coupling sleeve and the other of said wick sections also contacts the tapering internal bore.

2. The wick assembly of claim 1, wherein:

the second wick section comprises sand particles and a binder; and the first wick section is formed from a material selected from the group consisting of fibrous materials, wood products, plastic particles, and inorganic particles.

3. The wick assembly of claim 1, wherein the means for mounting comprises a radially extending flange adjacent an end of the sleeve and a cap ring positionable on the reservoir.

4. A wick assembly for use in a dispensing device that is capable of dispensing volatile material from a reservoir containing that volatile material, the wick assembly comprising:

a first wick section formed from a first material;

a second wick section formed from a second material that includes granules bound together by a binder and that is different from the first material, wherein the second wick section is positioned abutting against or adjacent to the first wick section;

a coupling sleeve for holding the second wick section against, or adjacent to, the first wick section so that ends of both the first and second wick sections terminate in the coupling sleeve and the coupling sleeve holds the wick sections in that abutting or adjacent relationship; and means for mounting the coupling sleeve to a reservoir so that the first wick section can extend into the reservoir;

wherein the means for mounting comprises a radially extending flange adjacent an end of the sleeve and a cap ring positionable on the reservoir;

wherein the cap ring has an annular depression for receiving the radially extending flange; and wherein one of said wick sections has an outer surface that forms an interference fit with an internal bore of the coupling sleeve and the other of said wick sections also contacts the internal bore.

5. The wick assembly of claim 4, wherein the cap ring is made of a plastic material.

6. A wick assembly for use in a dispensing device that is capable of dispensing volatile material from a reservoir containing that volatile material, the wick assembly comprising:

a first wick section formed from a first material;

a second wick section formed from a second material, wherein the second wick section is positioned abutting against or adjacent to the first wick section;

a coupling sleeve for holding the second wick section against, or adjacent to, the first wick section; and means for mounting the coupling sleeve to a reservoir so that the first wick section can extend into the reservoir, wherein the means for mounting comprises a cap ring positionable on the reservoir;

wherein the cap ring is integral with the first wick section in the sense of being formed as a single piece with the first wick section; and wherein one of said wick sections has an outer surface that forms an interference fit with an internal bore of the coupling sleeve and the other of said wick sections also contacts the internal bore.

7. The wick assembly of claim 1, in which both the first and second wick sections are essentially cylindrical.

8. The wick assembly of claim 7, wherein the second wick section has an end that is wider than an end of the first wick section.

9. The wick assembly of claim 1, wherein the first wick section is formed from a material selected from the group consisting of fibrous materials, wood products, thermoplastic particles and inorganic particles.

10. A wick assembly for use in a dispensing device that is capable of dispensing volatile material from a reservoir containing that volatile material, the wick assembly comprising:

a coupling sleeve;

a first wick section formed from a plastic material;

a second wick section formed from a composition comprising sand and a binder, wherein the second wick section is positioned abutting against or adjacent to the first wick section so that ends of both the first and second wick sections terminate in the coupling sleeve and the coupling sleeve holds the wick sections in an abutting or adjacent relationship;

wherein the coupling sleeve has a tapering internal bore and both the first and second wick sections terminate in the tapering internal bore; and wherein one of said wick sections has an outer surface that forms an interference fit with the internal bore of the coupling sleeve and the other of said wick sections also contacts the tapering internal bore.

11. A method for assembling a wick assembly, comprising:

obtaining wick assembly components comprising a reservoir, a cap ring, a first wick section made of a first material, a second wick section made of a second wick material that is different from the first material, and a coupling sleeve;

inserting the second wick section into the coupling sleeve such that an end of the second wick section terminates inside the coupling sleeve and an opposed end of the second wick section terminates outside the coupling sleeve;

inserting the first wick section into the cap ring so that an end of the first wick section terminates on one side of the cap ring, and an opposed end of the first wick section terminates on an opposed side of the cap ring; and assembling a sub-combination of the second wick section and coupling sleeve to a sub-combination of the first wick section and cap ring so that ends of both the first and second wick sections terminate in the coupling sleeve and the coupling sleeve holds the wick sections in an abutting or adjacent relationship;

wherein the coupling sleeve has a tapering internal bore and both the first and second wick sections terminate in the tapering internal bore; and wherein one of said wick sections has an outer surface that forms an interference fit with the internal bore of the coupling sleeve and the other of said wick sections also contacts the tapering internal bore.

* * * * *